(12) United States Patent
Bondinell et al.

(10) Patent No.: US 6,476,028 B1
(45) Date of Patent: Nov. 5, 2002

(54) COMPOUNDS AND METHODS

(75) Inventors: William E. Bondinell, Wayne, PA (US); James Chan, West Chester, PA (US); Roderick A. Porter, Ashwell near Baldock (GB); Joseph W. Venslavsky, Wayne, PA (US); Steven Dabbs, Harlow (GB); David T. Davies, Ware (GB)

(73) Assignees: SmithKline Beecham Corporation, Philadelphia, PA (US); SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/529,338
(22) PCT Filed: Oct. 7, 1998
(86) PCT No.: PCT/US98/21125
§ 371 (c)(1), (2), (4) Date: Aug. 8, 2000
(87) PCT Pub. No.: WO99/17773
PCT Pub. Date: Apr. 15, 1999

Related U.S. Application Data
(60) Provisional application No. 60/061,217, filed on Oct. 7, 1997.

(51) Int. Cl.[7] .............. A61K 31/53; A61K 31/44; C07D 481/00; C07D 401/00
(52) U.S. Cl. .............. 514/243; 514/246; 514/339; 544/183; 546/277.1; 546/277.7; 546/278
(58) Field of Search .............. 546/277.1, 277.7, 546/278.1; 544/183; 514/243, 246, 339

(56) References Cited

U.S. PATENT DOCUMENTS

| | | | |
|---|---|---|---|
| 4,278,677 A | 7/1981 | Nedelec et al. | 546/273 |
| 5,521,197 A | 5/1996 | Audia | 514/323 |
| 5,688,927 A | 11/1997 | Godiska et al. | 530/388.23 |

OTHER PUBLICATIONS

Taylor et al., Molecular determinants for recognition of RU24969 analogs at central 5–hydroxytryptamine recognition sites: Use of a Bilinear Function and Substituent Volumes to Describe Steric Fit, Mole. Pharm. 1988, vol. 34, pp. 42–52.

*Primary Examiner*—Alan L. Rotman
*Assistant Examiner*—Raymond Covington
(74) *Attorney, Agent, or Firm*—Nora Stein-Fernandez; Stephen A. Venetianer; Charles M. Kinzig

(57) ABSTRACT

A method of treating a CCR5-mediated disease state in mammals which comprises administering to a mammal in need of such treatment, an effective amount of a compound of formula (I) or a pharmaceutically acceptable salt thereof.

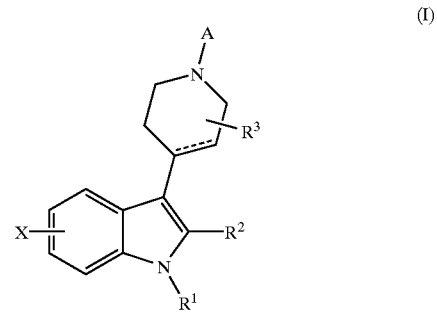

7 Claims, No Drawings

COMPOUNDS AND METHODS

This application is a 371 of PCT/US98/21125 filed Oct. 7, 1998 which claims the benefit of Ser. No. 60/061,217 filed Oct. 7, 1997.

FIELD OF THE INVENTION

This invention relates to substituted 3-(4-piperidinyl) indoles which are modulators, agonists or antagonists, of the CC chemokine receptor CC-CKR[5] now designated as CCR5 (*Nature Medicine*, 2: 1174–8, 1996). In addition, this invention relates to the treatment and prevention of disease states mediated by CCR5.

BACKGROUND OF THE INVENTION

T cells are not only key regulators of the immune response to infectious agents but are believed critical for the initiation and maintenance of the inflammatory reaction in a variety of chronic diseases. Increased numbers or enhanced activation state of T cells, especially CD4+ T cells, have been demonstrated in the synovium of individuals with rheumatoid arthritis (M. J. Elliott and R. N. Maini, *Int. Arch. Allergy Immunol.* 104: 112–1125, 1994), in the bronchial mucosa of asthmatics (C. J. Corrigan and A. B. Kay, *Immunol. Today* 13: 501–506, 1992), in the lesions of multiple sclerosis (R. Martin and H. F. McFarland, *Crit. Rev. Clin. Lab. Sci.* 32: 121–182, 1995), in psoriatic lesions (J. L. Jones, J. Berth-Jone, A. Fletcher and P. E. Hutchinson, *J. Pathol.* 174: 77–82, 1994) and in the fatty streaks of atherosclerosis (R. Ross, *Annu. Rev. Phvsiol.* 57: 791–804, 1995).

T cells, as well as other inflammatory cells, will migrate into tissues in response to the production of a variety chemotactic factors. Among these factors are a superfamily of 8–12 kDa proteins known as the chemokines. These proteins share structural features such as the presence of 3–4 conserved cysteine residues. RANTES, which stands for Regulated upon Activation Normal T cell Expressed and Secreted, is a 8 kDa protein member of CC branch of the chemokine family. These proteins recruit and activate immune and inflammatory cells through an interaction with G-protein coupled receptors. The CC branch is defined by the absence of an intervening amino acid residue between the first two cysteine residues and members of this family predominately elicit the migration of mononuclear cells, eosinophils and basophils (M. Baggiolini, B. Dewald, and B. Moser, *Adv. Immunol.* 55: 97–179, 1994; and J. J. Oppenheim, C. O. C. Zachariae, N. Mukaida, and K. Matsushima, *Annu. Rev. Immunol.* 9: 617–648, 1991).

RANTES potently produces chemotaxis of T cells, basophils, eosinophils, monocytes and mast cells. RANTES was originally identified as gene product induced late after antigen activation of T-cells (T. J. Schall, J. Jongstra, B. J. Dyer, J. Jorgensen, et al., *J. Immunol.* 141:1018–1025, 1988), however, RANTES has been shown to be synthesized and secreted by a diverse group of cells that include epithelial and endothelial cells (C. Stellato, L. A. Beck, G. A. Gorgone, D. Proud, et al., *J. Immunol.* 155: 410–418, 1995; and A. Marfaing-Koka, O. Devergne, G. Gorgone, A. Portier, et al., *J. Immunol.* 154: 1870–1878, 1994), synovial fibroblasts (P. Rathanaswami, M. Hachicha, M. Sadick, T. J. Schall, et al., *J. Biol. Chem.* 268: 5834–5839, 1993) and dermal fibroblasts (M. Sticherling, M. Kupper, F. Koltrowitz, E. Bornscheuer, et al., *J. Invest. Dermatol.* 105: 585–591, 1995), mesangial cells (G. Wolf, S. Aberle, F. Thaiss, et al., *Kidney Int.* 44: 795–804, 1994) and platelets (Y. Koameyoshi, A. Dorschner, A. I. Mallet, E. Christophers, et al., *J. Exp. Med.* 176: 587–592, 1992). In these cells, RANTES mRNA is rapidly upregulated in response to IL-1 or TNFα. Although RANTE mRNA is not usually detected in normal tissues (J. M. Pattison, P. J. Nelson, and A. M. Krensky, *Clin. Immunother.* 4: 1–8, 1995), increased mRNA or protein has been found in diseases characterized by a mononuclear infiltrate. For example, RANTES mRNA was visualized using in situ hybridization in renal allografts undergoing rejection (J. M. Pattison, P. J. Nelson, and A. M. Krensky, *Clin. Immunother.* 4: 1–8, 1995; and K. C. Nadeau, H. Azuma and N. I. Tilney, *Proc. Natl. Acad. USA* 92: 8729–8733, 1995) in the skin of atopic dermatitis patients after exposure to antigen (S. Ying, L. Taborda-Barata, Q. Meng, M. Humbert, et al., *J. Exp. Med.* 181: 2153–2159, 1995), and in endothelial cells of coronary arteries undergoing accelerated atherosclerosis after cardiac transplant (J. M. Pattison, P. J. Nelson, and A. M. Krensky, *Clin. Immunother.* 4: 1–8, 1995). Further, increased immunoreactive protein for RANTES has been detected in bronchoalveolar lavage fluid (R. Alam, J. York, M. Boyers, et al., *Am. J. Resp. Crit. Care Med.* 149: A951, 1994) and sputum from asthmatic individuals (C. M. Gelder, P. S. Thomas, D. H. Yates, I. M. Adcock, et al., *Thorax* 50: 1033–1037, 1995).

Several receptors have been identified that bind RANTES. In particular, CCR5, when expressed in either HEK 293 cells or CHO cells, binds RANTES. This receptor is expressed in T-cells and in monocytes and macrophages, immune/inflammatory cells which are important in the maintenance of a chronic inflammatory reaction. Pharmacological characterization of CCR5 indicates similarities to the RANTES binding site observed on isolated T cells. Therefore, antagonism of RANTES' action on CCR5, as well as antagonism of other natural modulators of CCR5, should inhibit the recruitment of T cells into inflammatory lesions and provide a novel therapeutic approach for the treatment of atopic and autoimmune disorders.

Since T cells express CCR5, receptor modulators of CCR5, particularly antagonists, are likely to provide beneficial effects in diseases including, but not limited to, asthma and atopic disorders (for example, atopic dermatitis and allergies), rheumatoid arthritis, atherosclerosis, psoriasis, sarcoidosis and other fibrotic diseases, autoimmune diseases such as multiple sclerosis, and inflammatory bowel disease, all in mammals, preferably humans. Furthermore, since CD8+ T cells have been implicated in COPD, CCR5 may play a role in their recruitment and therefore antagonists to CCR5 could provide potential therapeutic in the treatment of COPD. Also since CCR5 is a co-receptor for the entry of HIV into cells, receptor modulators may be useful in the treatment of HIV infection.

Surprisingly, it has now been discovered that a class of non-peptide compounds, in particular substituted 3-(4-piperidinyl)indoles of formula (I), function as CCR5 receptor modulators, and therefore, have utility in the treatment and prevention of disease states mediated by CCR5 receptor mechanisms.

SUMMARY OF THE INVENTION

In one aspect, the present invention is to a genus of novel compounds of formula (I), or pharmaceutically active salts thereof, said compounds which are also useful in treating the above-mentioned CCR5-mediated disease states:

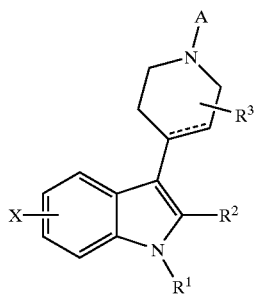

(I)

wherein:
- X is hydrogen or one or more of $C_{1-6}$alkyl, CONRR', trifluoromethyl, hydroxy, $C_{1-6}$alkoxy, benzyloxy, $C_{1-6}$alkylthio, or halo where R and R' are independently hydrogen or $C_{1-6}$alkyl;
- $R^1$ is hydrogen or $C_{1-6}$alkyl;
- $R^2$ is hydrogen or $C_{1-6}$alkyl;
- the dotted line, . . . , indicates a single bond or a double bond;
- $R^3$ is hydrogen or $C_{1-6}$alkyl;
- A is $[C(R")_2]_m CR"R^4R^5$ or $[C(R")_2]_n CR"=C R^4R^5$ where each R" is independently hydrogen or $C_{1-6}$alkyl;
- m is 0–3;
- n is 1–2
- $R^4$ is phenyl, biphenyl, naphthyl, 1-benzotriazinyl, or 2-benzotriazinyl, optionally substituted with one or more of $C_{1-6}$alkyl, cyano, trifluoromethyl, $NR^6R^7$, nitro, hydroxy, $C_{1-6}$alkoxy, benzyloxy, $C_{1-6}$alkylthio, or halo, where $R^6$ and $R^7$ are independently hydrogen or $C_{1-6}$alkyl;
- $R^5$ is R" when m is 0; alternatively, $R^5$ is R", phenyl or naphthyl when m is 1–3 or n is 1–2, wherein phenyl or naphthyl are optionally substituted with one or more of $C_{1-6}$alkyl, cyano, trifluoromethyl, $NR^6R^7$, nitro, hydroxy, $C_{1-6}$alkoxy, benzyloxy, $C_{1-6}$alkylthio, or halo.

In another aspect, the present invention is to a method of treating CCR5 mediated disease states, including, but not limited to, COPD, asthma and atopic disorders (for example, atopic dermatitis and allergies), rheumatoid arthritis, sarcoidosis and other fibrotic diseases, atherosclerosis, psoriasis, autoimmune diseases such as multiple sclerosis, inflammatory bowel disease, and HIV infection, ("CCR5-mediated diseases") all in mammals, preferably humans, comprising administering to such mammal in need thereof, a 3-(4-piperidinyl)indoles of formula (I), or pharmaceutically active salts thereof.

In yet another aspect, the present invention is to pharmaceutical compositions comprising a compound of formula (I) and a pharmaceutically acceptable carrier therefor. In particular, the pharmaceutical compositions of the present invention are used for treating CCR5-mediated disease states, including, but not limited to, COPD asthma and atopic disorders (for example, atopic dermatitis and allergies), rheumatoid arthritis, sarcoidosis and other fibrotic diseases, atherosclerosis, psoriasis, autoimmune diseases such as multiple sclerosis, inflammatory bowel disease, and HIV infection.

DETAILED DESCRIPTION OF THE INVENTION

It has now been discovered that substituted 3-(4-piperidinyl)indoles of formula (I) are CCR5 receptor modulators. It has also now been discovered that inhibition of CCR5 receptor mechanisms by treatment with the receptor modulators of formula (I), or a pharmaceutically acceptable salt thereof, represents a novel therapeutic and preventative approach to the treatment of a variety of disease states, including, but not limited to, asthma and atopic disorders (for example, atopic dermatitis and allergies), rheumatoid arthritis, sarcoidosis and other fibrotic diseases, atherosclerosis, psoriasis, autoimmune diseases such as multiple sclerosis, and inflammatory bowel disease, all in mammals, preferably humans. Furthermore, since CD8+ T cells have been implicated in COPD, CCR5 may play a role in their recruitment and therefore antagonists to CCR5 could provide potential therapeutic in the treatment of COPD. Also, since CCR5 is a co-receptor for the entry of HIV into cells, selective receptor modulators may be useful in the treatment of HIV infection.

The term "CCR5 mediated disease state" is used herein at all occurrences to mean any disease state which is mediated (or modulated) by CCR5.

Suitably, pharmaceutically acceptable salts of formula (I) include, but are not limited to, salts with inorganic acids such as hydrochloride, sulfate, phosphate, diphosphate, hydrobromide, and nitrate, or salts with an organic acid such as malate, maleate, fumarate, tartrate, succinate, citrate, acetate, lactate, methanesulfonate, p-toluenesulfonate, palmitate, salicylate, and stearate.

The compounds of the invention can exist in unsolvated as well as solvated forms, including hydrated forms. In general, the solvated forms, with pharmaceutically acceptable solvents such as water, ethanol, and the like, are equivalent to the unsolvated forms for purposes of this invention.

The compounds of the present invention may contain one or more asymmetric carbon atoms and may exist in racemic and optically active forms. The stereocenters may be (R), (S) or any combination of R and S configuration, for example, (R,R), (R,S), (S,S) or (S,R). All of these compounds are within the scope of the present invention.

For the compounds of formula (I) various embodiments are as follows.

- X is suitably hydrogen or one or more of $C_{1-6}$alkyl, CONRR', trifluoromethyl, hydroxy, $C_{1-6}$alkoxy, benzyloxy, $C_{1-6}$alkylthio, or halo where R and R' are independently hydrogen or $C_{1-6}$alkyl.
- $R^1$ is suitably hydrogen or $C_{1-6}$alkyl.
- $R^2$ is suitably hydrogen or $C_{1-6}$alkyl.
- $R^3$ is suitably hydrogen or $C_{1-6}$alkyl.
- A is suitably $[C(R")_2]_m CR"R^4R^5$ or $[C(R")_2]_n CR"=C R^4R^5$ where each R" is independently hydrogen or $C_{1-6}$alkyl.
- $R^4$ is suitably phenyl, biphenyl, naphthyl, 1-benzotriazinyl, or 2-benzotriazinyl, optionally substituted with one or more of $C_{1-6}$alkyl, cyano, trifluoromethyl, $NR^6R^7$, nitro, hydroxy, $C_{1-6}$alkoxy, benzyloxy, $C_{1-6}$alkylthio, or halo, where $R^6$ and $R^7$ are independently hydrogen or $C_{1-6}$alkyl
- $R^5$ is suitably R" when m is 0. Alternatively, $R^5$ is suitably R", phenyl or naphthyl when m is 1–3 or n is 1–2, wherein phenyl or naphthyl are optionally substituted with one or more of $C_{1-6}$alkyl, cyano, trifluoromethyl, $NR^6R^7$, nitro, hydroxy, $C_{1-6}$alkoxy, benzyloxy, $C_{1-6}$alkylthio, or halo.

As used herein, the term "halo" means all halogens, that is chloro, fluoro, bromo and iodo.

As used herein, the term "$C_{1-6}$alkyl" or "alkyl" means both straight and branched chain radicals of 1 to 6 carbon atoms, unless the chain length is otherwise limited, including, but not limited to, methyl, ethyl, n-propyl, iso-propyl, n-butyl, sec-butyl, iso-butyl, tert-butyl, and the like.

The term "$C_{1-6}$alkoxy" is used herein at all occurrences to mean a straight or branched chain radical of 1 to 6 carbon atoms, unless the chain length is limited thereto, bonded to an oxygen atom, including, but not limited to, methoxy, ethoxy, n-propoxy, isopropoxy, and the like.

The term "$C_{1-6}$alkylthio" is used herein at all occurrences to mean a straight or branched chain radical of 1 to 6 carbon atoms, unless the chain length is limited thereto, bonded to a sulfur atom, including, but not limited to, methylthio, ethylthio, and the like.

Known compounds that fall within the scope of this invention include compounds wherein A is $CH_2$-phenyl, the dotted line represents a double bond, $R^1$ and $R^2$ are hydrogen, and X is hydrogen, methoxy, 4-halo, 4-hydroxy, 5-methyl, 5-C(O)$NH_2$, 5-O$CH_2$Ph, or 7-ethyl; and wherein A is $CH_2$-phenyl, the dotted line represents a double bond, $R^1$ and $R^2$ are independently either hydrogen or methyl, and X is hydrogen; and wherein A is $CH_2$-phenyl, the dotted line represents a single bond, $R^1$ is hydrogen, $R^2$ is methyl, and X is hydrogen; and wherein A is $CH_2$-phenyl, the dotted line represents a double bond, $R^1$ is hydrogen, $R^2$ is methyl, $R^3$ is ethyl, and X is hydrogen; and wherein A is $CH_2$-phenyl, the dotted line represents a double bond, $R^1$ is hydrogen, $R^2$ is methyl, and X is 6-methoxy; and wherein A is 4-chlorobenzyl, the dotted line represents a double bond, $R^1$ and $R^2$ are hydrogen, and X is hydrogen; and wherein A is $CH_2CH_2$-phenyl, $R^1$, $R^2$ and $R^3$ are hydrogen, the dotted line represents either a single or double bond, and X is hydrogen, 5-methoxy, 5-C(O)$NH_2$, 5-benzyloxy, 5-chloro, 5-fluoro or 5-methyl; and wherein A is $(CH_2)_3$-phenyl, or A is $(CH_2)_4$-phenyl, or A is $CH_2$—$CH_2$-naphthyl, $R^1$, $R^2$ and $R^3$ are hydrogen, the dotted line represents either a single or double bond, and X is hydrogen, and wherein A is $CH_2CH_2$-Ph, $R^1$, $R^2$ and $R^3$ are hydrogen, the dotted line represents a single bond, and X is hydroxy; and wherein A is 2-(4-methoxyphenyl)ethyl, or A is 2-(4-fluorophenyl)ethyl, $R^1$, $R^2$ and $R^3$ are hydrogen, the dotted line represents a single bond, and X is 5-methoxy; and wherein X, $R^1$, $R^2$, and $R^3$ are each hydrogen, the dotted line represents a single bond, and A is 2-(4-ethoxyphenyl)ethyl, 2-([2,3 or 4]-methoxyphenyl)ethyl, 2-([2,3 or 4]-fluorophenyl)ethyl; 2-([2, 3 or 4-chlorophenyl)ethyl; 2-([2,3 or 4]-methylphenyl)ethyl, 2-([2 or 3]-trifluoromethylphenyl) ethyl, or 2-(4-bromophenyl)ethyl. See, for example, WO 9747302, published Dec. 18, 1997; EP 714894, published Jun. 5, 1996; Tetrahedron Letters, 1996, 52, pp. 10185—10192; and DE 2365967, published Feb. 10, 1977.

Among the preferred compounds of the invention are the following compounds:

5-chloro-3-[1-[3-(dimethylamino) phenylmethyl]-1,2,3,6-tetrahydro-4 -pyridinyl]-1H-indole;
3-[1,2,3,6-tetrahydro-1-(phenylmethyl)-4-pyridinyl]-1H-indol-5-ol;
3-[3-phenylpropyl)-4-piperidinyl]-H-indol-5-ol;
3-[1-(phenylmethyl)-4-piperidinyl]-1H-indol-5-ol;
3-[1-([1,1'-biphenyl]-2-ylmethyl)-4-piperidinyl]-1H-indol-5-ol;
3-[2-naphthalenylmethyl)-4-piperidinyl]-1H-indol-5-ol;
3-[1,1'-biphenyl]-4-ylmethyl)-4-piperidinyl]-1H-indol-5-ol;
3-[1-(4-phenylbutyl)-4-piperidinyl]1H-indol-5-ol;
3-[1-(3,3-diphenylpropyl)-4-piperidinyl]-1H-indol-5-ol;
3-[1-[4-(1,1-dimethylethyl)phenylmethyl)-piperidinyl]-1H-indol-5-ol;
3-[1,2,3,6-tetrahydro-1-(phenylmethyl)-4-pyridinyl]-1H-indole;
5-methoxy-3-[1,2,3,6-tetrahydro-1-(phenylmethyl)-4-pyridinyl]-1H-indole;
3-[1-[4-(2H-benzotriazin-2-yl)butyl]-4-piperidinyl]-1H-indol-5-ol;
3-[1-[4-(1H-benzotriazin-1-yl)butyl]-4-piperidinyl]-1H-indol-5-ol;
5-phenylmethoxy-3-[1,2,3,6-tetrahydro-1-(phenylmethyl)]-4-pyridinyl]-1H-indole;
3-[1-(4,4-diphenylbut-3-enyl)-4-piperidinyl]-1H-indol-5-ol;
3-[1-(3,3-diphenyl-2-propenyl)-4-piperidinyl]-1H-indol-5-ol; and
3-[1-(3,3-diphenylpropyl)-4-piperidinyl]-1H-indole.

Formulation of Pharmaceutical Compositions

The pharmaceutically effective compounds of this invention (and the pharmaceutically acceptable salts thereof) are administered in conventional dosage forms prepared by combining a compound of formula (I) ("active ingredient") in an amount sufficient to treat COPD, asthma and atopic disorders (for example, atopic dermatitis and allergies), rheumatoid arthritis, sarcoidosis and other fibrotic diseases, atherosclerosis, psoriasis, autoimmune diseases such as multiple sclerosis, inflammatory bowel disease, and HIV infection, with standard pharmaceutical carriers or diluents according to conventional procedures well known in the art. These procedures may involve mfixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1000 mg. When a liquid carrier is used, the preparation will be in the form of a syrup, emulsion, soft gelatin capsule, sterile injectable liquid such as an ampule or nonaqueous liquid suspension.

The active ingredient may also be administered topically to a mammal in need of treatment or prophylaxis of CCR5 mediated disease states. The amount of active ingredient required for therapeutic effect on topical administration will, of course, vary with the compound chosen, the nature and severity of the disease state being treated and the mammal undergoing treatment, and is ultimately at the discretion of the physician. A suitable dose of an active ingredient is 1.5 mg to 500 mg for topical administration, the most preferred dosage being 1 mg to 100 mg, for example 5 to 25 mg administered two or three times daily.

By topical administration is meant non-systemic administration and includes the application of the active ingredient externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous or alcoholic solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol. The formulation may incorporate any suitable surface active agent such as an anionic, cationic or non-ionic surfactant such as esters or polyoxyethylene derivatives thereof. Suspending agents such as natural gums, cellulose derivatives or inorganic materials such as silicaceous silicas, and other ingredients such as lanolin, may also be included.

The active ingredient may also be administered by inhalation. By "inhalation" is meant intranasal and oral inhalation administration. Appropriate dosage forms for such administration, such as an aerosol formulation or a metered dose inhaler, may be prepared by conventional techniques. The daily dosage amount of the active ingredient administered by inhalation is from about 0.1 mg to about 100 mg per day, preferably about 1mg to about 10 mg per day.

In one aspect, this invention relates to a method of treating asthma and atopic disorders (for example, atopic dermatitis and allergies), COPD, rheumatoid arthritis, sarcoidosis and other fibrotic diseases, atherosclerosis, psoriasis, autoimmune diseases such as multiple sclerosis, inflammatory bowel disease, and HIV infection, all in mammals, preferably humans, which comprises administering to such mammal an effective amount of a CCR5 receptor ligand, in particular, a compound as depicted in formula (I).

By the term "treating" is meant either prophylactic or therapeutic therapy. Such formula (I) compound can be administered to such mammal in a conventional dosage form prepared by combining the formula (I) compound with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. The formula (I) compound is administered to a mammal in need of treatment for CCR5-mediated diseases in an amount sufficient to decrease symptoms associated with these diseases. The route of administration may be oral or parenteral.

The term parenteral as used herein includes intravenous, intramuscular, subcutaneous, intra-rectal, intravaginal, intranasal or intraperitoneal administration. The subcutaneous and intramuscular forms of parenteral administration are generally preferred. The daily parenteral dosage regimen will preferably be from about 30 mg to about 300 mg per day of active ingredient. The daily oral dosage regimen will preferably be from about 100 mg to about 2000 mg per day of active ingredient.

It will be recognized by one of skill in the art that the optimal quantity and spacing of individual dosages of a formula (I) compound will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of the formula (I) compound given per day for a defined number of days, can be ascertained by those skilled in the art using conventional course of treatment determination tests.

Methods of Preparation

The compounds of formula (I) can be prepared by art-recognized procedures from known or commercially available starting materials, for example, by using the general procedures of Tetrahedron, 1996, 52, 10185–10192, U.S. Pat. No. 5,521,197, and Eur. J. Med. Chem., 1987, 22, 33–43.

For example, a suitably substituted indole 1-1, where X, $R^1$ and $R^2$ are defined in formula (I), which is commercially available or prepared by methods known to the art from commercially available starting materials, is condensed with a suitable 4-piperidone, for example, 1-benzyl-4-piperidone, using a suitable base, for example, sodium methoxide or potassium hydroxide, in a suitable solvent, for example, methanol, to give the 3-(1,2,3,6-tetrahydro-4-pyridinyl) indole 1-2, where D phenylmethyl, a compound of formula (I). Hydrogenation of 1-2, where D is phenylmethyl, with a suitable catalyst, for example, palladium-on-carbon, in a suitable solvent, for example, ethanol, for a suitable time, for example, 24 h, gives the 3-(4-piperidinyl)indole 1-3. Alkylation of 1-3 with a suitable reagent A-Y, where A is described in formula (I) and Y is a suitable leaving group, for example, chloro, bromo, iodo, methanesulfonyloxy, or toluenesulfonyloxy, with a suitable organic or inorganic base, for example, triethylamine, diisopropylethylamine, sodium carbonate, or potassium carbonate, in a suitable solvent, for example, acetone or dimethylformamide, affords compounds of formula (I) 1-4 where the dotted bond is a single bond. Alternatively, condensation of 1-1 with 4-piperidone affords 1-2, where D is hydrogen, which may be alkylated with A-Y to afford compounds of formula (I) 1-4 where the dotted bond is a double bond. Compounds 1-4 may also be obtained from 1-2 where D is hydrogen or from 1-3 by condensation with an appropriately substituted acid chloride to afford an amide which is reduced with an appropriated reagent, for example lithium aluminum hydride, in a suitable solvent, for example, tetrahydrofuran, to afford 1-4. If the starting materials are unavailable from a commercial source, their synthesis is described herein, or they can be prepared by procedures known in the art. More particularly, the compounds of this invention were prepared using the synthetic pathway illustrated in Scheme 1 shown below.

Scheme 1

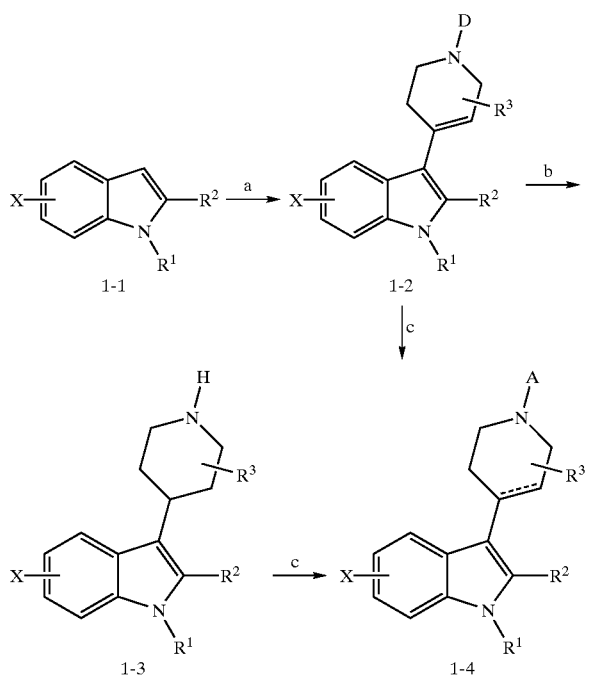

a) 1-benzyl-4-piperidone or 4-piperidone, $CH_3ONa$, $CH_3OH$, Δ, 16 h; b) $H_2$, 5% palladium-on-carbon, ethanol, 24 h; c) A-Y, triethylamine, acetone, Δ, 18 h.

Biological Data

CCR5 Receptor Binding Assay

CHO cell membranes ($0.25 \times 10^6$ cell equivalents) derived from CHO cells stably transfected with CCR5 were incubated with 0.3 $^{125}$I-RANTES in a 96 well plate for 45 min. at room temperature (final reaction volume 200 ul). The reaction was terminated by filtration and the filters (GF/C) were washed twelve times with a solution of phosphate buffered saline containing 0.1% bovine serum albumin and 0.05% $NaN_3$, The radioactivity bound to filters was measured by liquid scintillation spectrometry. Non-specific binding was determined in the presence of unlabelled RANTES (10 or 30 nM) and averages 30–50% of total binding.

CCR5 Receptor Functional Assay

The cellular functional assay used to assess antagonist activity of compounds was RANTES-induced $Ca^{2+}$ mobilization in RBL 2H3 cells stably expressing the hCCR5 receptor (RBL 2H3 hCCR5). Agonist activity is determined by $Ca^{2+}$ mobilization in the same cells which is inhibitable by a selective CCR5 antagonist. Cells were grown to 80–100% confluency in T-150 flasks and washed with phosphate-buffered saline. Cells were lifted from the flasks by treating with 3 mL of 1 mM EDTA for 3 min. at room temperature and diluting to $2 \times 10^6$ cells/mL with Krebs Ringer Henseleit buffer (KRH; 118 mM NaCl, 4.6 mM KCl, 25 mM $NaHCO_3$, 1 mM $KH_2PO_4$ and 11 mM glucose) containing 5 mM HEPES (pH 7.4), 1 mM $CaCl_2$, 1 mM $MgCl_2$ and 0.1% BSA and centrifuged at 200g for 3 min. Cells were resuspended at $2 \times 10^6$ cells/nL in the same buffer with 2 μM Fura-2AM, and incubated for 35 min. at 37° C. Cells were centrifuged at 200×g for 3 min. and resuspended in the same buffer without Fura-2AM, then incubated for 15 min. at 37° C. to complete the hydrolysis of intracellular Fura-2AM, and then centrifuged as before. Cells ($10_6$ cells/mL) were resuspended in cold KRH with 5 mM HEPES (pH 7.4), 1 mM $CaCl_2$, 1 mM $MgCl_2$ and 0.1% gelatin and maintained on ice until assayed. For antagonist studies, aliquots (2 mL) of cells were prewarmed at 37° C. for 5 min. in 3 mL plastic cuvettes and fluorescence measured in a fluorometer (Johnson Foundation Biomedical Group, Philadelphia, Pa., USA) with magnetic stirring and temperature maintained at 37° C. Excitation was set at 340 nm and emission set at 510 nm. Various concentrations of antagonists or vehicle were added and fluorescence monitored for ~15 sec to ensure that there was no change in baseline fluorescence, followed by the addition of 33 nM RANTES. Maximal $Ca^{2+}$ attained after 33 nM RANTES stimulation was calculated as described by Grynkiewicz er al., (1985). The percent of maximal RANTES-induced $Ca^{2+}$ was determined for each concentration of antagonist and the $IC_{50}$, defined as the concentration of test compound that inhibits 50% of the maximal 33 nM RANTES response, obtained from the concentration-response curves (5–7 concentrations of antagonists).

The compounds of this invention show CCR5 receptor modulator activity having $IC_{50}$ values in the range of 0.0001 to 100 μM. The full structure/activity relationship has not yet been established for the compounds of this invention. However, given the disclosure herein, one of ordinary skill in the art can utilize the present assays in order to determine which compounds of formula (I) are modulators of the CCR5 receptor and which bind thereto with an $IC_{50}$ value in the range of 0.0001 to 100 μM.

EXAMPLES

Example 1

Preparation of 3-[1-(3,3-Diphenylpropyl)-4-piperidinyl]-1H-indol-5-ol a) 5-Phenylmethoxy-3-[1,2,3,6-tetrahydro-1-(phenylmethyl) 4-pyridinyl]-1H-indole A slurry of 5-benzyloxyindole (6.85 g, 30.7 mmol) in methanol (50 mL) was added to a 25 wgt % solution of sodium methoxide in methanol (115 mL) at 5° C. under argon. 1-Benzyl-4-piperidone (5.8 g, 30.7 mmol) was added in one portion and the suspension heated at reflux for 16 h, cooled and diluted with a mixture of dichloromethane (100 mL) and methanol (150 mL). The solution was acidified to pH 5 with glacial acetic acid, concentrated to 100 mL, diluted with water (750 mL) and extracted with ethyl acetate (3×200 mL). The combined organic layers were washed with water (100 mL) and brine (100 mL) and dried ($Na_2SO_4$). Filtration and concentration in vacuo gave the title compound as a yellowrange solid (10.6 g, 87%). MS(ES) m/e 395.2 $[M+H]^+$.

b) 3-(4-Piperidinyl)-1H-indol-5ol

A mixture of the compound of Example 1(a) (1.0 g, 2.54 mmol) and 5% palladium-on-carbon (1.0 g) in absolute ethanol (200 mL) was hydrogenated at 50 psi for 24 h, filtered and concentrated in vacuo to give the title compound (0.52 g).

c) 3-[1-(3,3-Diphenylpropyl)-4-piperidinyl]-1H-indol-5-ol

A solution of the compound of Example 1(b) (0.44, 2.0 mmol), 1-bromo-3,3 diphenylpropane (0.56 g, 2.0 mmol) andtriethylamine (0.41g, 4.0 mmol) in acetone (75 mL) was heated at reflux for 18 h, cooled and concentrated in vacuo. The residue was partitioned between ethyl acetate (150 mL) and water (25 mL). The organic layer was washed with water (25 mL) and brine (25 mL), dried ($Na_2SO_4$), filtered and concentrated in vacuo. The residue was chromatographed (silica gel, 5% methanol/chloroform) to give the title compound (0.25 g). MS (EI) m/e 411.5 $[M+H]^+$.

Examples 2–6

Preparation of 3-[1-([1,1'-Biphenyl]-2-ylmethyl) 4piperidinyl]-1H-indol-5-ol and 3-1-([1,1'-Biphenyl]-4-yylmethyl)-4-piperidinyl]-1H-indol-5-ol and 3-[1-([2-Naphthalenylmethyl)-4-piperidinyl]-1H-indol-5-ol and 3-[1-(3-Phenylpropyl)-4-piperidinyl]-1H-indol-5-ol and 3-[1-(4-Phenylbutyl)-4-piperidinyl]-1H-indol-5-ol Following the general procedure of Example 1(c), except substituting the appropriate aralkyl halide for 1-bromo-3,3-diphenylpropane, gave the title compounds:

3-[1-([1,1'-biphenyl]-2-ylmethyl)]-4-piperidinyl]-1H-indol-5-ol: MS(EI) m/e 382 $[M]^+$;

3-[1-([1,1'-biphenyl]-4-ylmethyl)]-4-piperidinyl]-1H-indol-5-ol : MS(FAB) m/e 383 $[M+H]^+$;

3-[1-(2-naphthalenylmethyl)-4-piperidinyl]-1H-indol-5-ol: MS(FAB) nme 357 $[M+H]^+$;

3-[1-(3-phenylpropyl)-4-piperidinyl]-1H-indol-5-ol: MS(EI) m/e 334 $[M]^+$; and

3-[1-(4-phenylbutyl)-4-piperidinyl]-1H-indol-5-ol: MS(EI) m/e 348 $[M]^+$.

Examples 7–8

Preparation of 3-[1-(Phenylmethyl)-4-piperidinyl]-1H-indol-5-ol and 3-[1-[4-(1,1-Dimethylethyl) phenylmethyl]-piperidinyl]-1H-indol-5-ol Following the general procedure of Example 1(c), except substituting benzyl bromide and 4tert-butylbenzyl bromide for 1-bromo-3,3-diphenylpropane and butanone for acetone, afforded the title compounds:

3-[1-(phenylmethyl)-4-piperidinyl]-1H-indol-5-ol: MS(EI) m/e 306 $[M]^+$; and

3-[1-[4-(1,1-dimethylethyl) phenylmethyl]-4-piperidinyl]-1H-indol-5-ol: MS(EI) m/e 362 $[M]^+$.

Examples 9–10

Preparation of 3-[1-(3,3-Diphenyl-2-propenyl)-4-piperidinyl]-1H-indol-5-ol and 3-[1-(4,4-Diphenylbut-3enyl)-4-piperidinyl]-1H-indol-5-ol Using the procedure of Example 1(c), except substituting 3,3-diphenyl-2-propenyl bromide (J. Med. Chem., 1967, 10, 627–635) or 4,4-diphenyl-3-butenyl bromide (J. Med. Chem., 1967, 10, 627–635) for 1-bromo-3,3-diphenylpropane, gave the title compounds:

3-[1-(3,3-diphenyl-2-propenyl)-4-piperidinyl]-1H-indol-5ol: MS(ES) m/e 409.3 $[M+H]^+$; and 3-[1-(4,4-diphenylbut-3-enyl)-4-piperidinyl]-1H-indol-5-ol: MS(ES) m/e 423.3 $[M+H]^+$.

Example 11

Preparation of 3-[1-(3,3-Diphenylpropyl)-4-piperidinyl]-1H-indole

Using the procedure of Example 1(a)–(c), except substituting indole for 5-benzyloxyindole, gave the title compound. MS(ES) tre 395.3 [M+H]+.

Example 12

Preparation of 3-[1,2,3,6-Tetrahydro-1-(phenylmethyl)-4-pyridinyl]-1H-indol-5-ol A mixture of 5-hydroxyindole (0.66 g) and 1-benzyl-4-piperidone (0.95 g) in glacial acetic acid was purged with nitrogen and heated to reflux for 50 min. The mixture was concentrated in vacuo, treated with toluene and concentrated in vacuo, and the residue was purified by chromatography (silica gel, 20–30% ethanol/dichloromethane) to afford the title compound which was recrystallized from ethanol (0.4 g). mp 223–227° C.

Example 13

Preparation of 5-Chloro-3-[1-[3-(dimethylamino) phenylmethyl]-1,2,3,6-tetrahydro4-pyridinyl]-1H-indole a) 5-Chloro-3-[1[3-(dimethylamino)benzoyl]-1,2,3,6-tetrahydro-4-pyridinyl]-1H-indole A mixture of 5-chloro-3-(1,2,3,6-tetrahydro-4-pyridinyl)-1H-indole (0.53 g, 2.3 mmol) (Eur. J. Med. Chem., 1987, 22, 33–43) and 3-(dimethylamino)benzoyl chloride (0.5 g, 2.3 mmol) (Chem. Pharm. Bull., 1980, 28, 2045–2051) in tetrahydrofuran was stirred and treated with triethylamine (0.64 mL, 2 eq). The mixture was stirred for 2 h, treated with aqueous sodium bicarbonate (50 mL) and extracted with ethyl acetate. The organic phase was washed with brine and dried ($Na_2SO_4$) to give the title compound (0.83 g).

b) 5-Chloro-3-[1-[3-(dimethylamino)phenylmethyl]-1,2,3,6-tetrahydro-4-pyridinyl]-1H-indole A mixture of the compound of Example 13(a) (0.82 g, 2.1 mmol) and lithium aluminum hydride (0.8 g, 2 mmol) in tetrahydrofuran (50 mL) was stirred and heated to reflux for 4 h. The mixture was cooled and carefully treated with 10% sodium hydroxide (12 mL), water (3 mL), and ether (100 mL). The organic phase was dried ($Na_2SO_4$), concentrated in vacuo, and the residue was chromatographed (silica gel, 4% methanol/dichloromethane). Fractions containing the title compound were pooled, concentrated in vacua, and the residue was recrystallized from ethyl acetate/methanol to give the title compound (0.55 g). mp 193–195° C.

Example 14

Preparation of 3-[1-[4-(2H-Benzotriazin-2-yl)butyl-4-piperidinyl-1H-indol-5-ol

A mixture of the compound of Example 1(b) (0.11 g), 2-(4-bromobutyl)-2H-benzotriazole (0.11 g) (J. Med.

Chem., 1994, 37, 2754–2760) and sodium bicarbonate (0.10 g) in dimethylformamide (1 mL) was heated at 80° C. for 16 h. The mixture was diluted with ethyl acetate (10 mL) and washed with water (5×5 mL). The organic phase was dried (MgSO$_4$) and concentrated in vacuo. The residue was chromatographed (silica gel, step gradient, 0–10% ethanol/dichloromethane) to give the title compound (0.08 g). mp(ethyl acetate) 205–206° C.

Example 15

Preparation of 3-[1-[4-(1H-Benzotriazin-1-yl)butyl]-4-piperidinyl]-1H-indol-5-ol Following the procedure of Example 14, except substituting, 1-(4-bromobutyl)-1H-benzotriazole (J. Med. Chem., 1994, 37, 2754–2760) for 2-(4-bromobutyl)-2H-benzotriazole, gave the title compound. mp 179–180° C.

All publications, including, but not limited to, patents and patent applications cited in this specification, are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration it is believed that one skilled in the art can, given the preceding description, utilize the present invention to its fullest extent. Therefore any examples are to be construed as merely illustrative and not a limitation on the scope of the present invention in any way. The embodiments of the invention in which an exclusive property or privilege is claimed are defined as follows.

What is claimed is:

1. A method of treating a CCR5-mediated disease state in mammals which comprises administering to a mammal in need of such treatment, an effective amount of a compound of formula (I) or a pharmaceutically acceptable salt thereof:

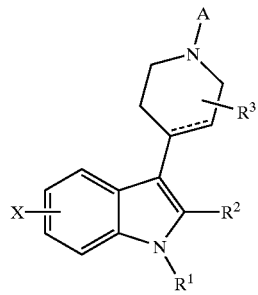

(I)

wherein:
X is hydrogen or one or more of $C_{1-6}$alkyl, CONRR', trifluoromethyl, hydroxy, $C_{1-6}$alkoxy, benzyloxy, $C_{1-6}$alkylthio, or halo where R and R' are independently hydrogen or $C_{1-6}$alkyl;
$R^1$ is hydrogen or $C_{1-6}$alkyl;
$R^2$ is hydrogen or $C_{1-6}$alkyl;
the dotted line, . . . , indicates a single bond or a double bond;
$R^3$ is hydrogen or $C_{1-6}$alkyl;
A is $[C(R")_2]_m CR"R^4R^5$ or $[C(R")_2]_n CR"=C R^4R^5$ where each R" is independently hydrogen or $C_{1-6}$alkyl;
m is 0–3;

n is 1–2
$R^4$ is phenyl, biphenyl, naphthyl, 1-benzotriazinyl, or 2-benzotriazinyl, optionally substituted with one or more of $C_{1-6}$alkyl, cyano, trifluoromethyl, $NR^6R^7$, nitro, hydroxy, $C_{1-6}$alkoxy, benzyloxy, $C_{1-6}$alkylthio, or halo, where $R^6$ and $R^7$ are independently hydrogen or $C_{1-6}$alkyl;
$R^5$ is R' when m is 0; alternatively, $R^5$ is R", phenyl or naphthyl when m is 1–3 or n is 1–2, wherein phenyl or naphthyl are optionally substituted with one or more of $C_{1-6}$alkyl, cyano, trifluoromethyl, $NR^6R^7$, nitro, hydroxy, $C_{1-6}$alkoxy, benzyloxy, $C_{1-6}$alkylthio, or halo.

2. The method as claimed in claim 1 wherein the compound of formula (I) is a compound selected from:
5-chloro-3-[1-[3-(dimethylamino)phenylmethyl]-1,2,3,6-tetrahydro-4-pyridinyl]-1H-indole;
3-[1,2,3,6-tetrahydro-1-(phenylmethyl)-4-pyridinyl]-1H-indol-5-ol;
3-[1-(3-phenylpropyl)-4-piperidinyl]-1H-indol-5-ol;
3-[1-(phenylmethyl)-4-piperidinyl]-1H-indol-5-ol;
3-[1-([1,1'-biphenyl]-2-ylmethyl)]-4-piperidinyl]-1H-indol-5-ol;
3-[1-(2-naphthalenylmethyl)-4-piperidinyl]-1H-indol-5-ol;
3-[1-([1,1'-biphenyl]4-ylmethyl)]-4-piperidinyl]-1H-indol-5-ol;
3-[1-(4-phenylbutyl)-4-piperidinyl]-1H-indol-5-ol;
3-[1-(3,3-diphenylpropyl)-4-piperidinyl]-1H-indol-5-ol;
3-[1-[4-(1,1-dimethylethyl)phenylmethyl]-4-piperidinyl]-1H-indol-5-ol,
3-[1,2,3,6-tetrahydro-1-(phenylmethyl)-4-pyridinyl]-1H-indole;
5-methoxy-3-[1,2,3,6-tetrahydro-1-(phenylmethyl)-4-pyridinyl]-1H-indole;
3-[1-[4-(2H-benzotriazin-2-yl)butyl]-4-piperidinyl]-1H-indol-5-ol;
3-[1-[4-(1H-benzotriazin-l-yl)butyl]-4-piperidinyl]-1H-indol-5-ol;
5-phenylmethoxy-3-[1,2,3,6-tetrahydro-1-(phenylmethyl)-4-pyridinyl]-1H-indole;
3-[-(4,4diphenylbut-3-enyl)-4-piperidinyl]-1H-indol-5-ol;
3-[1-(3,3-diphenyl-2-propenyl)-4-piperidinyl]-1H-indol-5-ol; and
3-[1-(3,3-diphenylpropyl)-4-piperidinyl]-1H-indole.

3. The method as claimed in claim 1, wherein the disease is selected from COPD, asthma and atopic disorders, rheumatoid arthritis, sarcoidosis, fibrotic diseases, atherosclerosis, psoriasis, autoimmune diseases, multiple sclerosis, inflammatory bowel disease, and HIV infection.

4. The method as claimed in claim 1 wherein the compound of formula (I) is a compound selected from:
5-chloro-3-[1-[3-(dimethylamino)phenylmethyl]-1,2,3,6-tetrahydro-4-pyridinyl]-1H-indole
3-[1-([1,1'-biphenyl]-2-ylmethyl)]-4-piperidinyl]-1H-indol-5-ol;
3-[1-([1,1'-biphenyl]-4-ylmethyl)]-4-piperidinyl]-1H-indol-5-ol;
3-[1-(3,3-diphenylpropyl)-4-piperidinyl]-1H-indol-5-ol;
3-[1-[4-(2H-benzotriazin-2-yl)butyl]-4-piperidinyl]-1H-indol-5-ol;
3-[1-[4-(1H-benzotriazin-1-yl)butyl]-4-piperidinyl]-1H-indol-5-ol;

3-[1-(4,4-diphenylbut-3-enyl)-4-piperidinyl]-1H-indol-5-ol;

3-[1-(3,3-diphenyl-2-propenyl)-4piperidinyl]-1H-indol-5-ol; and

3-[1-(3,3-diphenylpropyl)-4-piperidinyl]-1H-indole.

5. The method as claimed in claim 4, wherein the disease is selected from COPD, asthma and atopic disorders, rheumatoid arthritis, sarcoidosis and other fibrotic diseases, atherosclerosis, psoriasis, autoimmune diseases such as multiple sclerosis, inflammatory bowel disease, and HIV infection.

6. A compound selected from:

5-chloro-3-[1-[3-(dimethylamino)phenylmethyl]-1,2,3,6-tetrahydro-4-pyridinyl]-1H-indole;

3-[1-([1,1'-biphenyl]-2-ylmethyl)]-4-piperidinyl]-1H-indol-5-ol;

3-[1-([1,1'-biphenyl]4-ylmethyl)]-4-piperidinyl]-1H-indol-5-ol;

3-[1-(3,3-diphenylpropyl)4-piperidinyl]-1H-indol-5-ol;

3-[1-[4-(2H-benzotriazin-2-yl)butyl]-4-piperidinyl]-1H-indol-5-ol;

3-[1-[4-(1H-benzotriazin-1-yl)butyl]-4-piperidinyl]-1H-indol-5-ol;

3-[1-(4,4-diphenylbut-3-enyl)-4-piperidinyl]-1H-indol-5-ol;

3-[1-(3,3-diphenyl-2-propenyl)-4-piperidinyl]-1H-indol-5-ol; and

3-[1-(3,3-diphenylpropyl)-4-piperidinyl]-1H-indole.

7. A pharmaceutical composition comprising a compound according to claim 6, and a pharmaceutically acceptable carrier.

* * * * *